US006436244B1

(12) United States Patent
Führer et al.

(10) Patent No.: US 6,436,244 B1
(45) Date of Patent: Aug. 20, 2002

(54) PROCESS FOR THE ELUTION OF FLUORINATED EMULSIFIERS

(75) Inventors: Stephan Führer, Kastl; Gernot Löhr, Burgkirchen; Werner Schwertfeger, Altötting, all of (DE)

(73) Assignee: Dyneon GmbH (DE)

( * ) Notice: Subject to any disclaimer, the term of this patent is extended or adjusted under 35 U.S.C. 154(b) by 0 days.

(21) Appl. No.: 09/608,973

(22) Filed: Jun. 30, 2000

(30) Foreign Application Priority Data

Jul. 14, 1999 (DE) .......................... 199 32 771

(51) Int. Cl.$^7$ .......................... B01D 3/38; B01D 15/04; C02F 1/42; C07L 51/42
(52) U.S. Cl. .................. 203/95; 203/DIG. 25; 210/664; 210/683; 554/154; 554/195; 554/201; 560/227; 535/605; 535/608
(58) Field of Search ................ 203/92, 95–96, 203/34, DIG. 25; 560/227; 554/184–185, 193, 195, 154, 201; 210/664, 683; 562/605, 608, 113; 523/310; 528/482, 502

(56) References Cited

U.S. PATENT DOCUMENTS

| 3,882,153 A | 5/1975 | Seki et al. | .................. 554/184 |
| 4,005,137 A | * 1/1977 | Rudolph et al. | ............. 260/539 |
| 4,609,497 A | * 9/1986 | Cope | .......................... 562/605 |

FOREIGN PATENT DOCUMENTS

| EP | 0 014 431 B1 | 1/1980 | ............ B01J/49/00 |
| EP | 0 632 009 B1 | 5/1994 | ........... C07C/53/50 |
| WO | WO 99/62830 | 12/1999 | ............. C02F/1/58 |
| WO | WO 99/62858 | 12/1999 | ........... C07C/51/47 |

* cited by examiner

Primary Examiner—Virginia Manoharan
(74) Attorney, Agent, or Firm—Dean M. Harts; James V. Lilly

(57) ABSTRACT

Fluorinated emulsifier acids bound to an anion exchanger resin can be eluted using a mixture of water, a compound of the formula M—X, in which M is an alkali metal or an alkylammonium ion, and X is hydroxyl, fluoride or chloride, and at least one organic solvent which completely dissolves the other components. For work-up of the eluent, this is advantageously subjected to steam distillation until all volatile constituents have been essentially removed, and the emulsifier acid is liberated from the steam distillation residue using a sufficiently strong acid. This emulsifier acid can advantageously be distilled off and collected as the ammonium salt in aqueous ammonia solution.

13 Claims, No Drawings

PROCESS FOR THE ELUTION OF FLUORINATED EMULSIFIERS

DESCRIPTION

The invention relates to a process for the elution of fluorinated emulsifiers from anion exchanger resins, to corresponding mixtures for carrying out this process, and to the further work-up of the eluate.

In particular, the invention relates to a process for the elution of fluorinated emulsifiers bound to an anion exchanger resin, in which the resin is brought into contact with a mixture essentially consisting of a) water, b) a compound of the formula

in which M is an alkali metal or alkylammonium ion, and X is hydroxyl, fluoride or chloride, and c) at least one organic solvent which completely dissolves the other components a) and b) and thus provides a sufficient quantity of anions $X^-$ for the elution of the emulsifiers from the anion exchanger resin.

The mixture for the elution preferably essentially consists of, in percent by weight, a) from 15 to 40% of water, b) from 1 to 10 of the compound M—X, and c) from 60 to 70% of the solvent.

A particularly preferred mixture essentially consists of a) from 18 to 35% of water, b) from 2 to 8% of M—X, and c) from 60 to 70% of solvent.

Preferred solvents, which can be employed individually or as a mixture, are alkanols having 1 to 4 carbon atoms, acetone, mono- and dialkyl ethers of monoglycol and diglycol, where the term alkyl groups here is taken to mean methyl or ethyl. Particularly preferred solvents are methanol, dimethyl monoglycol ether and dimethyl diglycol ether.

Preferred cations $M^+$ are lithium, sodium, potassium, tetramethylammonium and tetraethylammonium, and the preferred anion $X^-$ is hydroxyl. Surprisingly, particularly effective aqueous solutions are those of alkali metal hydroxides and alkylammonia.

The fluorinated emulsifiers to be eluted have been known for some time and are employed, in particular, in the polymerization of fluorinated olefins since they do not act as telogens. They are essentially fluorinated alkanecarboxylic and -sulfonic acids, in which the alkyl radical is partially or preferably fully fluorinated and is generally linear or terminally branched. Particular preference is given to perfluorooctanoic acid, referred to below as PFOA, where this abbreviation should hereinafter also be taken to mean the other conventional fluorinated emulsifiers.

The recovery of PFOA using anion exchanger resins has been known for some time and is described, for example, in U.S. Pat. No. 3,882,153 and in EP-B-0 014 431. Particularly advantageous recovery methods for PFOA from waste water are described in WO-A-99/62858 and WO-A-99/62830.

Anion exchanger resins are very effective in removing PFQA from aqueous systems. Highly basic anion exchanger resins, in particular, remove PFOA virtually quantitatively from waste water and similar solutions. In practice, more than 95% of the PFOA present can be recovered in this way. The full capacity of the ion exchanger can be utilized.

However, the strength of the adsorption of the PFOA to the exchanger resin makes elution more difficult. For example, if a loaded, highly basic anion exchanger is eluted with a one-molar, aqueous solution of ammonia, sodium hydroxide or potassium fluoride, PFOA concentrations in the eluate in the order of only 0.1 mmol/l are obtained. However, work-up of such considerable volumes of waste water is not economical.

On the other hand, weakly basic anion exchanger resins are not as efficient in the recovery of PFOA from the aqueous system. Thus, these resins exhibit premature "diffuse" break-through, i.e. the PFOA is released back into the treated aqueous system in small amounts. It is thus not possible to reduce the PFOA reliably to levels below about 5 ppm (corresponding to $7.5 \cdot 10^{-6}$ mol/l) from large volumes of waste water. Such low concentrations are desired for environmental protection reasons since PFOA has poor biodegradability. This applies in particular to waste water containing nonionic emulsifiers, as employed, for example, in concentration by ultrafiltration (EP-B-0 632 009).

In the process disclosed in EP-B-0 014 431, the PFOA is eluted from the anion exchanger using a mixture of a water-soluble solvent, such as methanol, and small amounts of a mineral acid, such as sulfuric acid or hydrochloric acid. In this way, an eluate containing up to 400 mmol/l of PFOA is obtained using a mixture of 89% by weight of methanol, 4% by weight of sulfuric acid and 7% by weight of water. The eluate usually separates into two layers, the lower layer essentially consisting of PFOA and the upper layer corresponding approximately to the elution mixture. On a larger scale, however, this phase separation does not occur reliably, meaning that recovery of the upper phase for elution is not readily possible (and thus, for example, makes a continuous process more difficult). For regeneration of the ion exchanger resin, about 5 bed volumes of eluate mixture are required, which in practice means from about 5 to 10 $m^3$ of eluate mixture which is a fire risk. The associated equipment complexity is considerable.

By contrast, the above-mentioned mixture, which does not have these disadvantages, is employed for the elution in accordance with the invention. In addition, the process according to the invention allows simple and effective work-up of the eluent, which is firstly subjected to steam distillation until it is essentially free from volatile substances, after which the emulsifier acid in the steam distillation residue is liberated using a sufficiently strong acid. The liberated and thus free (emulsifier) acid is then advantageously distilled off and expediently collected in aqueous ammonia solution since the emulsifier acid is usually employed in the form of the ammonium salt in the polymerization of the fluorinated olefins.

The invention thus relates to an economical process which can be controlled reliably on a large scale for the elution of fluorinated emulsifiers and their recovery in such pure form that they satisfy the requirements made for use in polymerization.

The invention is explained in greater detail in the examples below.

EXAMPLES

The elution power of the following elution mixtures was measured by determining the concentration of PFOA in the eluate after the first bed volume of the elution mixture had flowed through the ion exchanger column. The column had a length of 30 cm and a diameter of 6.5 cm and was filled with 400 ml of the commercially available anion exchanger resin ®AMBERLITE 402 (highly basic). The resin was charged with an ammonium perfluorooctanoate (APFOA) solution (commercial product from 3M with the trade name FC 143) until break-through and washed with 2 l of deionized water.

After 600 ml of the eluate mixture had flowed through the column, a sample was taken and the content of PFOA analyzed by conversion into the methyl ester with analysis by gas chromatography using an internal standard. The detection limit here was 5 ppm.

In the examples below, the content of PFOA is given in ppm. The elution rate was 200 ml/h.

The composition of the elution mixtures is given in percent by weight. None of the elution mixtures employed had a miscibility gap. Unless otherwise specified, the elution was carried out at room temperature.

Comparative Example (room temperature)

Elution of PFQA with aqueous solutions.

| Eluent (water) | 1 mol/l NaOH | 1 mol/l NH$_3$ | 1 mol/l KF |
|---|---|---|---|
| Concentration of PFOA in eluate in ppm | 20 | 17 | 160 |

EXAMPLES 1 to 3

Elution with aqueous/organic solutions.

An elution concentration of APFOA of greater than 30 000 ppm is regarded as industrially acceptable.

EXAMPLE 1

| Composition [% by weight] | NaOH | 5.0 | 5.0 | 1.0 | 5.0 |
|---|---|---|---|---|---|
| | NH$_3$ | — | — | — | 1.7 |
| | H$_2$O | 25.0 | 45.0 | 26.1 | 23.3 |
| | CH$_3$OH | 70.0 | 50.0 | 72.9 | 70.0 |
| Elution temperature | | Concentration of PFOA in eluate in ppm | | | |
| Room temperature | | 15000 | 2900 | 8400 | 62000 |
| 40° C. | | 54000 | 7300 | 13000 | 79000 |
| 50° C. | | 52000 | — | — | — |

EXAMPLE 2

| Composition [% by weight] | NH$_3$ | 2.5 | [(CH$_3$)$_4$N]OH | 3.1 | 6.2 |
|---|---|---|---|---|---|
| | H$_2$O | 7.5 | H$_2$O | 31.6 | 24.8 |
| | CH$_3$OH | 90.0 | CH$_3$OH | 65.3 | 70.0 |
| Elution temperature | | Concentration of PFOA in eluate in ppm | | | |
| Room temperature | | 2100 | | 67000 | 150000 |
| 40° C. | | 2800 | | 57000 | — |
| 50° C. | | 3100 | | — | — |

EXAMPLE 3

| Composition [% by weight] | NaOH | 4.6 | 4.1 | 4.6 | 3.7 | 4.6 |
|---|---|---|---|---|---|---|
| | H$_2$O | 22.7 | 19.4 | 22.7 | 26.7 | 22.7 |
| | CH$_3$OH | 63.6 | 35.3 | 63.6 | 32.2 | 63.6 |
| | OS2 *) | 9.1 ME | 41.1 ME | 9.1 DE | 37.4 DE | 9.1 Ac |
| Concentration PFOA in eluate in ppm | | 170000 | 140000 | 33000 | 57000 | 26000 |

*)OS2 = second organic solvent
ME = dimethyl monoglycol ether
DE = dimethyl diglycol ether
Ac = acetone

What is claimed is:

1. A process for elution of a fluorinated emulsifier bound to an anion exchanger resin, wherein the resin is brought into contact with a mixture consisting essentially of:
    a) water,
    b) a compound of the formula $$M\text{---}X$$

in which M is an alkali metal or alkylammonium ion, and X is hydroxide, fluoride or chloride, and
    c) at least one organic solvent which completely dissolves the other components a) and b) and thus provides a sufficient quantity of anions X$^-$ for elution of the emulsifier from the anion exchanger resin.

2. The process as claimed in claim 1, in which the mixture consists essentially of, in percent by weight, of
    a) from 15 to 40% of water,
    b) from 1 to 10% of the compound M—X, and
    c) from 60 to 70% of solvent.

3. The process as claimed in claim 2, in which the mixture consists essentially of:
    a) from 18 to 35% of water, b) from 2 to 8% of the compound M—X, and f) from 60 to 70% of solvent.

4. The process as claimed in any one of claims 1–3, in which the solvent is selected from at least one of the group consisting of alkanols having 1 to 4 carbon atoms, acetone, and mono- and dialkyl ethers of moonoglycol and diglycol wherein the alkyl ether is methyl or ethyl.

5. The process as claimed in claim 4, wherein the solvent is at least one of methanol, dimethyl mnonoglycol ether, or dimethyl diglycol ether.

6. The process as claimed in claim 1, where M in the compound M—X is lithium, sodium, potassium, tetramethylammonium or tetraethylammonium, and X is hydroxide.

7. The process as claimed in claim 1, wherein component b) is an ammoniacal alkali metal hydroxide solution.

8. The process of claim 1, wherein the fluorinated emulsifier is fluorinated alkane carboxylic or sulfonic acid.

9. A process for the work-up of an eluate comprising:
    a) providing a fluorinated emulsifier bound to an anion exchange resin;
    b) contacting the resin with a mixture consisting essentially of:
       i) water,
       ii) a compound of the formula $$M\text{---}X$$

in which M is an alkali metal or alkylammonium ion, and X is OH, F, or Cl, and
       iii) at least one organic solvent which completely dissolves the other components
       i) and ii) and thus provides a sufficient quantity of anions X$^-$ for elution of the emulsifier from the resin;
    c) subjecting the eluate to steam distillation until the eluate is essentially free from volatile constituents; and d) treating the steam distillation residue with an acid sufficiently strong to liberate a free acid form of the emulsifier.

10. The process of claim 9 further comprising the step of recovering the emulsifier as an ammonium salt of the free acid form of the emulsifier in an aqueous ammonia solution.

11. The process of claim 9 wherein the solvent is selected from at least one of the group consisting of alkanols having 1 to 4 carbon atoms, acetone, and mono- and dialkyl ethers of monoglycol and diglycol, and wherein the alkyl ether is methyl or ethyl.

12. The process of claim 9, where the solvent is methanol, a mixture of methanol and dimethyl monoglycol ether, or a mixture of methanol and dimethyl diglycol ether.

13. The process of claim 9, wherein the fluorinated emulsifier is perfluorooctanoic acid.

\* \* \* \* \*

UNITED STATES PATENT AND TRADEMARK OFFICE
CERTIFICATE OF CORRECTION

PATENT NO. : 6,436,244 B1
DATED : August 20, 2002
INVENTOR(S) : Fuehrer, Stephan It is certified that error appears in the above-identified patent and that said Letters Patent is hereby corrected as shown below:

Column 1,
Line 63, delete "PFQA" and insert in place thereof -- PFOA --

Column 3,
Line 19, delete "PFQA" and insert in place thereof -- PFOA --

Column 4,
Line 34, delete "f)" and insert in place thereof -- c) --
Line 38, delete "moonoglycol" and insert in place thereof -- monoglycol --
Line 41, delete "mnonoglycol" and insert in place thereof -- monoglycol --

Signed and Sealed this

Fourth Day of March, 2003

JAMES E. ROGAN
*Director of the United States Patent and Trademark Office*